(12) United States Patent
Li et al.

(10) Patent No.: US 8,605,980 B2
(45) Date of Patent: Dec. 10, 2013

(54) METHOD AND APPARATUS USING MAGNETIC RESONANCE IMAGING FOR CANCER IDENTIFICATION

(75) Inventors: Xin Li, Beaverton, OR (US); Charles S. Springer, Jr., Portland, OR (US); William D. Rooney, Lake Oswego, OR (US); Wei Huang, Lake Oswego, OR (US); Jingang Xu, Hillsboro, OR (US); Ian J. Tagge, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 401 days.

(21) Appl. No.: 13/125,485

(22) PCT Filed: May 7, 2009

(86) PCT No.: PCT/US2009/043201
§ 371 (c)(1),
(2), (4) Date: Apr. 21, 2011

(87) PCT Pub. No.: WO2010/051065
PCT Pub. Date: May 6, 2010

(65) Prior Publication Data
US 2011/0201917 A1    Aug. 18, 2011

Related U.S. Application Data

(60) Provisional application No. 61/171,411, filed on Apr. 21, 2009, provisional application No. 61/110,404, filed on Oct. 31, 2008.

(51) Int. Cl.
*G06K 9/00*    (2006.01)

(52) U.S. Cl.
USPC .......................................... 382/133; 382/128

(58) Field of Classification Search
None
See application file for complete search history.

(56) References Cited

U.S. PATENT DOCUMENTS

| | | | | |
|---|---|---|---|---|
| 6,611,778 | B2 * | 8/2003 | Degani | 702/104 |
| 7,603,157 | B2 * | 10/2009 | Feiweier et al. | 600/410 |
| 8,126,222 | B2 * | 2/2012 | Kohle | 382/128 |
| 8,175,355 | B2 * | 5/2012 | El Fakhri et al. | 382/128 |
| 8,280,488 | B2 * | 10/2012 | Huisman et al. | 600/420 |
| 2004/0242994 | A1 | 12/2004 | Brady et al. | |
| 2004/0252994 | A1 * | 12/2004 | Bickham et al. | 398/26 |
| 2007/0230757 | A1 | 10/2007 | Trachtenberg et al. | |
| 2008/0125643 | A1 | 5/2008 | Huisman et al. | |

* cited by examiner

*Primary Examiner* — Nancy Bitar
(74) *Attorney, Agent, or Firm* — Schwabe, Williamson & Wyatt

(57) ABSTRACT

Embodiments provide a Magnetic Resonance Imaging (MRI) technique and optionally software—collectively referred to as the "shutter-speed" model—to analyze image data of cancer patients. Embodiments provide a minimally invasive, yet precisely accurate, approach to determining whether tumors are malignant or benign by distinguishing the characteristics of contrast reagent activity in benign and malignant tumors. Exemplary embodiments provide MRI measured biomarkers for tumor malignancy determination, effectively eliminating or limiting the false positives suffered by existing MRI techniques.

20 Claims, 5 Drawing Sheets

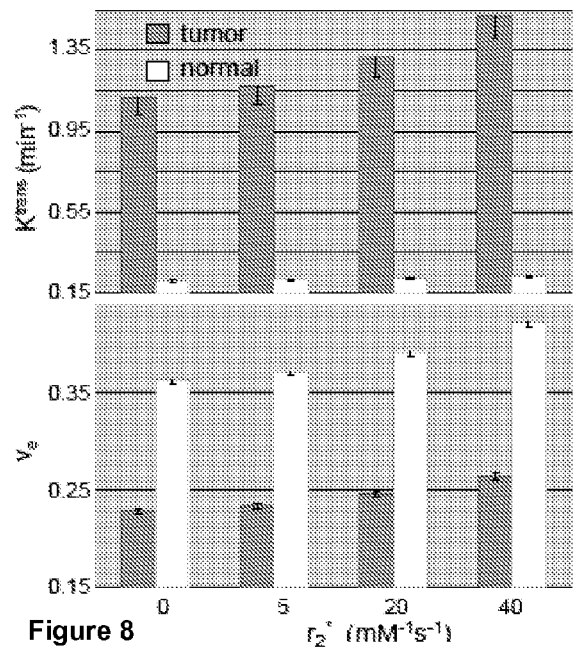
Figure 8
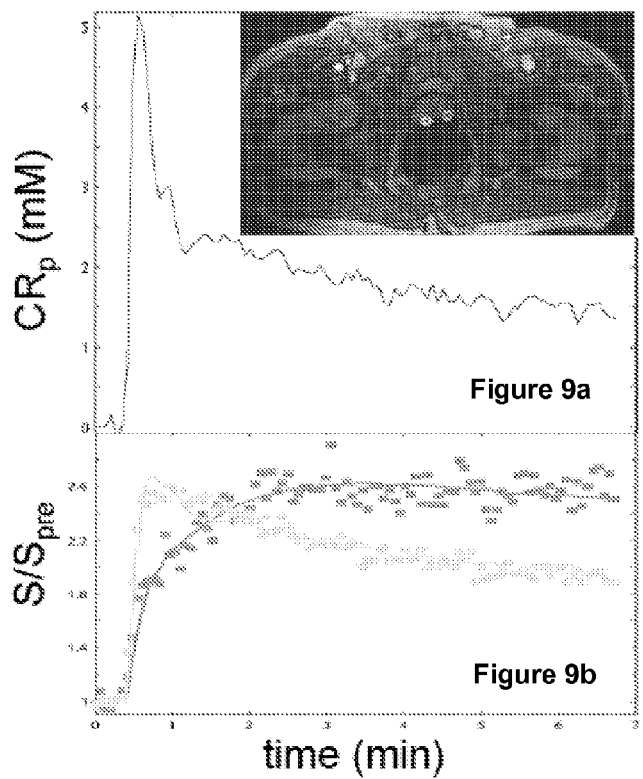
Figure 9a
Figure 9b
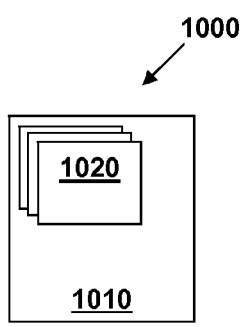
Figure 10

METHOD AND APPARATUS USING MAGNETIC RESONANCE IMAGING FOR CANCER IDENTIFICATION

CROSS REFERENCE TO RELATED APPLICATIONS

The present application claims priority to U.S. Provisional Patent Application No. 61/171,411, filed Apr. 21, 2009, entitled "DCE-MRI Water Signal Analysis for Improved Cancer Identification" and to U.S. Provisional Patent Application No. 61/110,404, filed Oct. 31, 2008, entitled "MRI Biomarker for Cancer Identification," the entire disclosures of which are hereby incorporated by reference in their entirety.

GOVERNMENT INTERESTS

This invention was made with Government support under Grant Nos. RO1-NS40801 and RO1-EB00422 awarded by The National Institutes of Health. The Government has certain rights in the invention.

TECHNICAL FIELD

Embodiments herein relate to identification of cancer, and, more specifically, to methods and apparatus using magnetic resonance imaging for cancer identification.

BACKGROUND

Screening for breast cancer represents one of modern medicine's success stories. However, the continued large fraction of false positives in current diagnostic protocols often leads to biopsy/pathology procedures that cause considerable pain, anxiety, healthcare cost, and possibly increased malignancy risk, but which are potentially avoidable. To address this problem, there have been recent calls for the increased use of magnetic resonance imaging (MRI) in breast screening.

The problems associated with false positive results are not unique to breast cancer screening. Other cancers suffer from large numbers of false positive results, causing significant stress as well as often requiring additional costly and painful procedures to confirm or deny the initial results.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 8 illustrates how the $K^{trans}$ (volume fraction CR transfer rate constant product, top) and $v_e$ (extracellular, extravascular space, EES, volume fraction, bottom) fitting results would change if increasing interstitial $^1H_2O\,T_2^*$ quenching is assumed.

FIG. 9a (inset) shows a transverse pelvic DCE image slice (anterior up/inferior perspective, ~34 seconds post CR injection) of a research subject. Two ROIs are indicated within the prostate gland: one in an area of retrospectively-confirmed prostate cancer, left; and the other in contralateral normal-appearing prostate tissue, right. FIG. 9a plots the arterial input function obtained from an ROI in a femoral artery. Its magnitude was adjusted using a custom-written numerical approach and an obturator muscle ROI for reference tissue. The time-course from the first-pass was used to estimate blood volume fraction. Color-matched tissue data time-courses (points) and representative fittings (curves) are seen in FIG. 9b.

FIG. 10 illustrates an article of manufacture in accordance with an embodiment herein.

DETAILED DESCRIPTION OF DISCLOSED EMBODIMENTS

Figure 1:
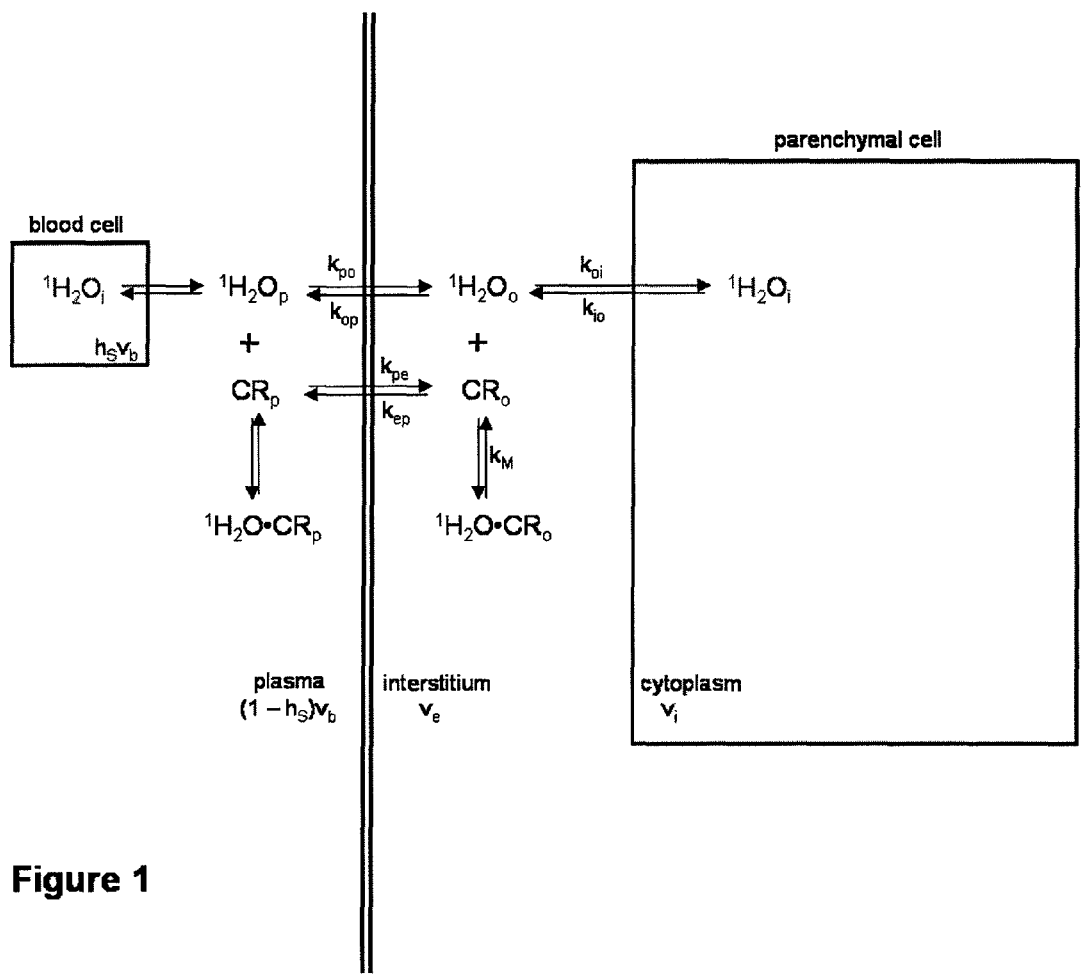
FIG. 1 illustrates the pharmacokinetic modeling scheme for DCE-MRI in accordance with various embodiments. The three general compartments for contrast reagent (CR) and for water (blood, interstitium, and parenchymal cytoplasmic) are illustrated—though not in relative proportions to their volume fractions ($v_b$, $v_e$, and $v_i$). The pertinent chemical equilibria and their unidirectional rate constants are indicated as well.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, methods, apparatuses, and systems using magnetic resonance imaging for cancer identification are provided. In exemplary embodiments, a computing device may be endowed with one or more components of the disclosed apparatuses and/or systems and may be employed to perform one or more methods as disclosed herein.

Embodiments herein provide a Magnetic Resonance Imaging (MRI) technique and optionally newly developed software—collectively referred to as the "shutter-speed" model—to analyze image data of cancer patients. Embodiments provide a minimally invasive, yet precisely accurate, approach to determining whether tumors are malignant or benign. Exemplary embodiments provide MRI measured biomarkers for tumor malignancy determination, effectively solving the false positive riddle from which current MRI techniques suffer.

Although some embodiments throughout are described with reference to breast cancer or prostate cancer, the methods and apparatuses described herein may be utilized for other cancers, such as brain, esophageal, leg osteosarcoma, etc. as well as for any Dynamic-Contrast-Enhanced Magnetic Resonance Imaging (DCE-MRI) analysis where water exchange effects are relevant, including tissue differential/ disease state analysis of the brain (Alzheimers, MS, etc.), muscles (such as heart), etc., and quantitative vascular phenotype mapping.

"Quantitative MRI" produces parametric maps of MR, patho-physiological, and/or pharmacokinetic biomarker properties. The DCE-MRI sub-category is particularly significant because it applies to a wide pathology range. In DCE-MRI, the $T_1$-weighted tissue $^1H_2O$ MRI signal intensity is acquired before, during, and after the (usually) bolus injection of a hydrophilic, paramagnetic contrast reagent (CR). The CR passage through a tissue region-of-interest (ROI) can cause a transient increase of the longitudinal $^1H_2O$ relaxation rate constant $[R_1 \equiv (T_1)^{-1}]$ with consequent elevated MR steady-state signal intensity. This elevation may be identified on the MR image.

In DCE-MRI, the neglect of intercompartmental water exchange kinetics considerations can lead to systematic errors in parameters extracted by quantitative analyses. Examples here are the compartmental water mole fractions defining tissue spaces. Therefore, DCE-MRI is also a sub-category of in vivo MR "molecular imaging"—mapping the distribution and/or activity of molecules in living tissues.

In essence, in embodiments, the CR plays the role of the nuclear medicine radioactive tracer. However, in nuclear medicine, the tracer is detected directly (by its radioactivity in disintegrations per second (dps)—the amount of tracer present in the tissue, but compartmental localization is not intrinsic to the signal). In contrast, the MRI CR is detected indirectly, via its interaction with water and effect on the nature of tissue $^1H_2O$ relaxation (so the water interaction with the CR is what is directly traced). Beneficially, the CR is not radioactive. Also, MRI involves no ionizing radiation.

Affecting the recovery of longitudinal $^1H_2O$ magnetization (i.e., in the magnetic field direction) requires (transient) water CR molecular interaction, as depicted in FIG. 1. The three major loci for tissue water, the cytoplasmae, the interstitium, and the blood, are indicated with subscripts i, o (or e), and b (p, for plasma), respectively. There are water binding equilibria depicted in each compartment in which the CR is thought to enter. The compartmental volume fractions are designated as $v_i$, $v_e$, and $v_b$, respectively, though the relative areas in FIG. 1 are not proportional.

The CR and water molecules are never equally distributed in tissue. Therefore, the only way that most water (cytoplasmic) can access CR is via exchange equilibria across cytolemmae and blood vessel walls. These are indicated in FIG. 1 with the unidirectional rate constants, $k_{oi}$, $k_{io}$, and $k_{po}$, $k_{op}$, respectively. In existing methods, tracer pharmacokinetic models are applied directly to MRI data—such methods are referred to here as the Standard Model (SM). However, this results in the constraint that all inter-compartmental equilibrium water exchange processes be treated as if infinitely fast ($k_{oi}+k_{io} \to \infty$, and $k_{po}+k_{op} \to \infty$). This is not valid, and the assumption may effectively "short circuit" MRI determination of CR compartmentalization—the pharmacokinetic essence. In accordance with embodiments herein, the incorporation of equilibrium water exchange MR effects into pharmacokinetic derivation is referred to herein as the Shutter-Speed Model (SSM). This is accomplished by allowing $k_{oi}+k_{io}$ and $k_{po}+k_{op}$ to be finite.

The SM assumes that water exchange between cells and/or blood and the interstitial spaces is effectively infinitely fast (in the fast exchange limit—FXL). However, when CR is passing through the tumor tissue, the water exchange systems can depart from this fast exchange limit due to the interaction with the CR (and therefore enter into a fast-exchange regime— FXR). This happens for both benign and malignant tumors; however, the exchange difference between FXL and FXR, as far as $K^{trans}$ is concerned, is significantly greater for malignant tumors as opposed to benign tumors. For benign tumors, the exchange difference is typically below 0.025 min$^{-1}$, whereas for malignant tumors, the exchange difference is typically above 0.025 min$^{-1}$. This differentiating line provides a threshold against which the obtained values may be compared to classify a tumor or tissue sample. In embodiments, a threshold may be established at an exchange difference (delta $K^{trans}$) of 0.02 to 0.03 min$^{-1}$.

While a single threshold is mentioned above, in embodiments, more than one delta $K^{trans}$ threshold may be established. For example, a first threshold may be established that is intended to include all or a substantial percentage of the malignant tissues above the threshold. A secondary threshold may be established at a lower delta $K^{trans}$ value with an intention of included all true positive indicators. However, a lower threshold may introduce a larger number of false positives. For a tissue having a delta $K^{trans}$ value residing between the first and second threshold, additional analysis may be utilized to further classify the tissue.

In an embodiment, the shutter-speed model (SSM) accounts for the FXR (therefore including equilibrium exchange effects when the CR passes through) and thus is better able to pick up the "leaky blood vessel" effect which is common in malignant tumors. At a maximum level of CR in the interstitial space, an interstitial water molecule in a benign lesion may typically encounter a CR molecule an average of 60 times before it enters a cell, whereas in a malignant tumor this may happen 260 times on average (4+ times as often). If that difference is neglected (which the standard model does), then it is sufficient to cause significant $K^{trans}$ (the volume-weighted CR extravasation rate constant) underestimations in malignant tumors. Because $K^{trans}$ values are greater for malignant tissues than for benign tissues, if $K^{trans}$ is underestimated, then it may make a malignant tumor seem benign (false negative) or vice versa a benign tissue appear to be malignant (false positive). The SSM model accounts for this difference, and by using the delta $K^{trans}$ (change in $K^{trans}$) as well as the $K^{trans}$ to $k_{ep}$ comparison, classification of tumors may be accomplished. In accordance with an embodiment, $k_{ep}$ is the unidirectional CR intravasation rate constant—it is $K^{trans}$ divided by the $v_e$ (the extracellular, extravascular volume fraction available to the contrast agent molecule). The pharmacokinetic analysis of DCE-MRI data yields $K^{trans}$ and $k_{ep}$.

In accordance with an embodiment, the difference in $K^{trans}$ returned by SSM, as compared to the Standard Model analyses, offers a very high degree of tumor differentiation (i.e., specificity). It is a measure of the shutter-speed effect, which is disproportionally present and important in malignant tumors, that permits differentiation of benign and malignant tumors. The increased permeability of malignant tumor blood vessels exceeds a threshold above which exchange kinetics become influential. This amplification is measured by the delta $K^{trans}$ biomarker, and accounts for the high SSM specificity.

Figure 2:
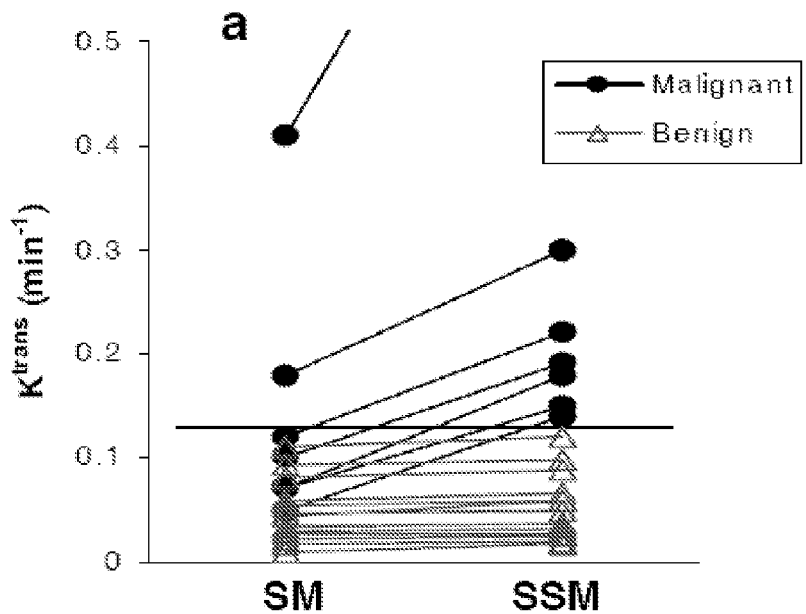
FIG. 2 illustrates $K^{trans}$ values obtained by a Standard Model and by a Shutter-Speed Model in accordance with embodiments herein.

In analyses of DCE-MRI data from patients with suspicious breast lesions initially ruled positive by institutional screening protocols, the SM $K^{trans}$ values for benign and malignant lesions exhibit considerable overlap. The Shutter-Speed Model (SSM) may allow for finite exchange kinetics thus agreeing with the SM $K^{trans}$ value for each of the benign lesions. However, it reveals that the SM underestimates $K^{trans}$ for each of the malignant tumors in this population. FIG. 2 illustrates $K^{trans}$ values obtained by both SM and SSM, and shows how SSM recognizes a difference in $K^{trans}$ between benign and malignant tissue. The fact that this phenomenon is unique to malignant tumors allows their discrimination from the benign lesions, as validated by comparison with gold standard pathology analyses of subsequent biopsy tissue samples to which the MRI analyses were blinded. Likewise, the SM overestimates $k_{ep}$, particularly for the benign tumors. Thus, incorporation of the SSM into the screening protocols may preclude the need for the biopsy/pathology procedures that otherwise would yield benign findings.

Thus, in embodiments, two binary classifiers have been developed:

1. "delta$K^{trans}$"—the change in $K^{trans}$; thresholds may be established with the goal/intention of including all true positives. Thresholds may be established as desired to distinguish/classify the tissues/tumors. In an embodiment, further analysis may be conducted via a secondary mapping algorithm (plot of ($K^{trans}$ VS. $k_{ep}$) to allow for a second determination with respect to those points that are somewhat unclear or fall below a determined threshold.

2. The use of 2D plots ($K^{trans}$ vs. $k_{ep}$), where the radius of a circle centered at the origin of the plot may be used as a "binary classifier." In embodiments, the radius of the circle may be used as a threshold to distinguish benign from malignant tumors. Such a threshold may be established at approximately 0.2 min$^{-1}$, for example, from 0.19 min$^{-1}$ to 0.25 min$^{-1}$.

In embodiments, an MRI examination aided by SSM analysis may provide a clearer diagnosis and may be an intermediate step between a mammographic scan and a biopsy intervention if breast cancer is suspected from both the mammogram and the MRI results. Adding this intermediate diagnostic step may greatly reduce or eliminate the number of unnecessary (and possibly all) biopsy surgeries and also reduce the pain, stress and expense for most patients.

It is important to note that the SSM is a generalization of the SM. That is, the SM is but a special case of the SSM. Thus, if the shutter-speed effect is negligible in any tissue, the program will automatically perform a SM analysis. One can test this by computationally constraining the SSM analysis to a SM form. If there is no difference from the result obtained when the SSM analysis is given free rein, then there is no significant shutter-speed effect for that tissue. In the case of breast tumors, this is the case for the $K^{trans}$ biomarker in only benign lesions. However, there is a shutter-speed effect for the $v_e$ biomarker in benign breast lesions, and it is about the same size as in malignant tumors.

To test SSM, SSM was employed to analyze MR images of 22 women volunteers who had previously screened positive for breast cancer by mammography and/or clinical examination. The shutter-speed software operates by using a complex mathematical formula to track the passage of injected contrast dye through a tumor area. Contrast dyes are commonly used in medical imaging to increase the visibility of tissue abnormalities.

When viewed through the shutter-speed analysis, the MRI data suggested that only seven of the 22 women actually had malignant tumors. These projections were later shown to be 100 percent accurate after each of the study participants underwent subsequent biopsies for pathology determinations. Typically, 75 percent of mammographically-indicated biopsies yield negative pathology results, meaning that an intermediate step such as an MRI determination could greatly reduce or eliminate the number of unnecessary biopsy surgeries.

Figure 3:
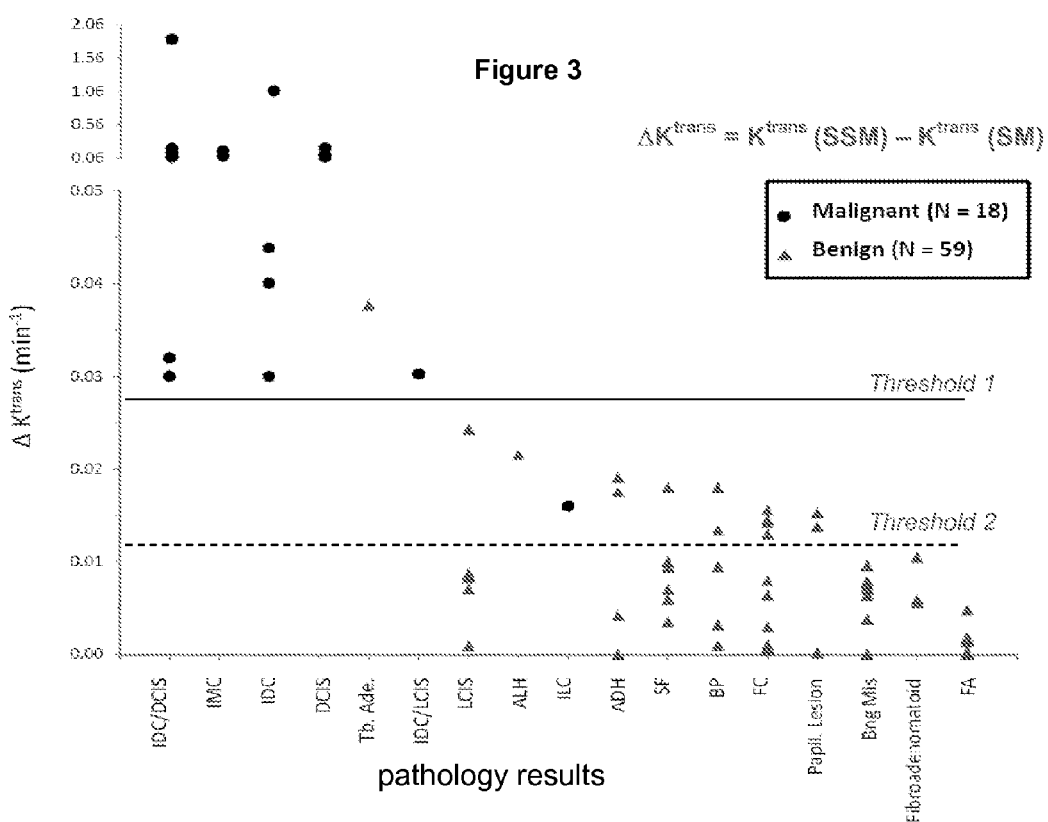
FIG. 3 illustrates delta $K^{trans}$ results of a 77 lesion data set (from 74 patients).

This population study has been expanded to include 77 breast tumors (in 74 patients) and, with the mapping provision for one rare type of malignant tumor, maintains 100% specificity. FIG. 3 illustrates delta $K^{trans}$ results of the 74 patient data set illustrating 77 lesions.

In addition, FIG. 3 illustrates the multiple threshold concept described previously. The first threshold is intended to capture all or a substantial percentage of the malignant tissues above the threshold. The first delta $K^{trans}$ threshold may be set, for example, between 0.02 min$^{-1}$ and 0.03 min$^{-1}$. The secondary threshold is established at a lower delta $K^{trans}$ value with an intention of included all true positive indicators. The second delta $K^{trans}$ threshold may be set, for example, between 0.01 min$^{-1}$ and 0.02 min$^{-1}$. For a tissue having a delta $K^{trans}$ value residing between the first and second threshold, additional analysis may be utilized to further classify the tissue. Such analysis may include heat map analysis of regions of interest to better classify the tissue.

Figure 4:
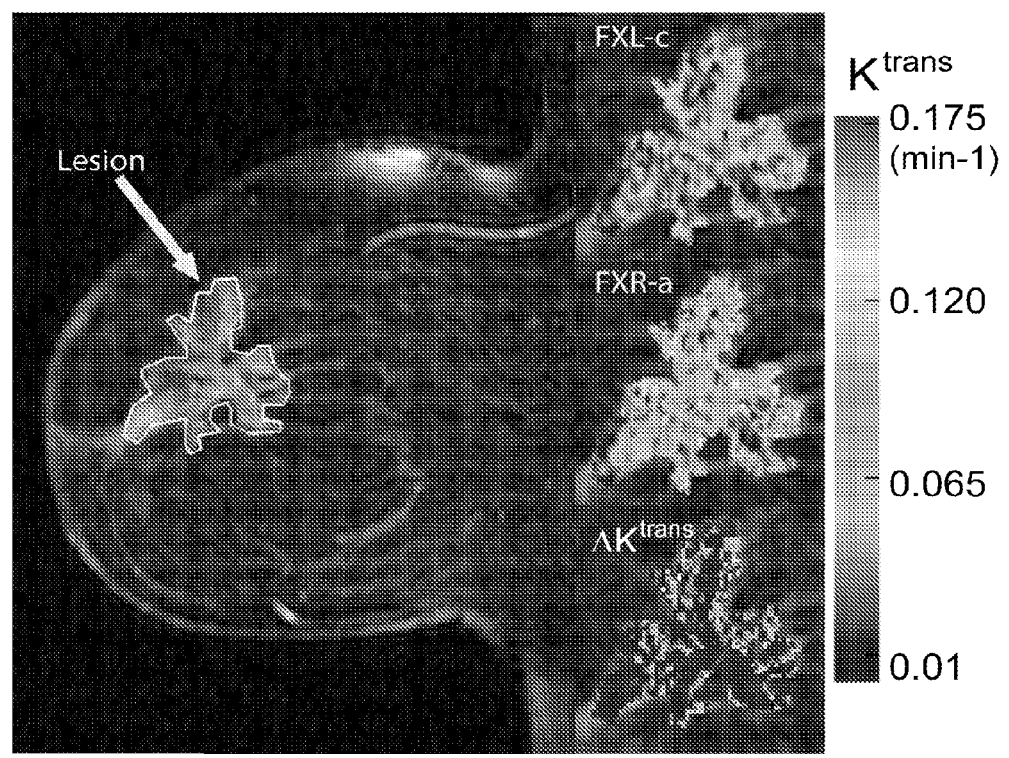
FIG. 4 illustrates a heat map analysis of a region of interest (ROI), as delineated at the left.

FIG. 4 illustrates a heat map analysis of a ROI, as delineated at the left. The three maps to the right show the results of various analyses of the ROI. At the top, the SM (FXL-c) image is shown which does not provide an indicator of malignancy. The middle image represents the SSM (FXR-a) image, which indicates some areas of interest. However, the lower image, representing the delta $K^{trans}$ value, clearly outlines the particular areas of concern within the ROI. Even though this lesion is fairly early stage, the delta $K^{trans}$ analysis provides an indicator of the tumor malignancy. While in some situations the identification of the tumor malignancy may not result in treatment, the early identification enables the tumor growth to be tracked over a period of time.

For the more limited data set (22 patients), data were obtained with consent from patients with positive mammographic and/or clinical MRI reports from standard, institutional breast cancer workups and protocols. All had MRI contrast-enhanced lesions radiologically classified as BIRADS (Breast Imaging Reporting and Data System) four (B-4, suspicious) or five (B-5, highly suggestive of malignancy). Emphasizing practicability and robustness, the data are of a rather routine clinical nature (and they were obtained at two different institutions, with two different instruments, CRs, etc.): the two different data acquisitions were not optimized for DCE-MRI. For example, though the spatial resolution is reasonable, the temporal resolution is not optimal. Of particular interest is the fact that the adipose tissue—$^1H_2C$-MR signal was suppressed in the acquisitions at one institution, while at the other institution it was not.

Figure 5:
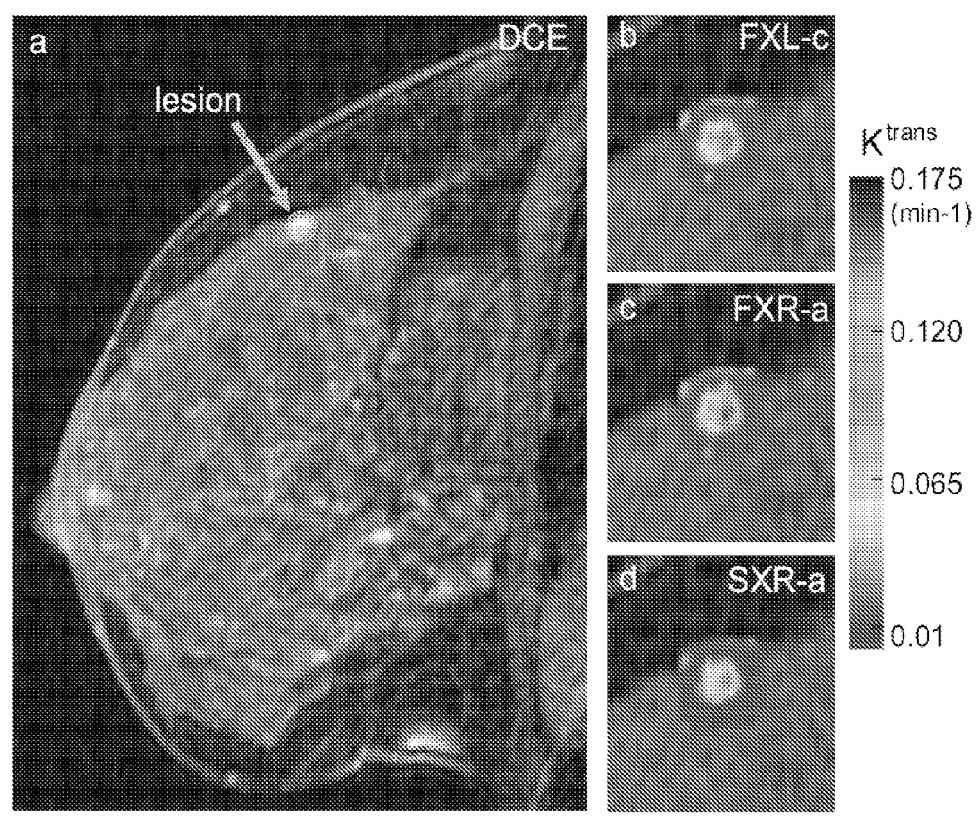
FIGS. 5a, 5b, 5c, and 5d illustrate a sagittal, fat-suppressed breast DCE-MRI image (FIG. 5a) containing a malignant invasive ductal carcinoma (IDC) tumor (circled contrast-enhanced region-of-interest). Pharmacokinetic $K^{trans}$ parametric maps of the tumor, generated by the Standard Model (FXL-constrained) and two members of the Shutter-Speed Model family (FXR-allowed) and (SXR-allowed), are shown in FIG. 5b, FIG. 5c, and FIG. 5d, respectively.

FIG. 5a shows the DCE pharmacokinetic image of sagittal slice 16 (numbering from lateral to medial) of the left breast of a 52 year-old patient, obtained 2.6 minutes after CR injection. It was acquired with adipose —$^1H_2C$-suppression (required in the institutional protocol). In contrast to those with no fat suppression, this darker image shows glandular regions brighter than fatty tissue. The ROI circumscribes the enhanced lesion evident in this slice, subsequently found to be a malignant invasive ductal carcinoma (IDC) by pathology analysis. Each of the 22 patients participated in a DCE-MRI acquisition subsequent to her clinical mammography and/or MRI screening but prior to the biopsy procedure and the pathology analysis.

Additional DCE-MRI acquisition details may be found in Li, et al., Dynamic NMR Effects in Breast Cancer Dynamic-Contrast-Enhanced MRI, PNAS, Vol. 105, No. 46, 17937-17942 (2008) (and Supporting Online Material), the entire disclosures of which are incorporated by reference in their entirety. For each of the 22 subjects, ROI DCE-MRI time-course data were analyzed from one sagittal image slice (out of 16 to 40 per breast) that exhibited a lesion to be subsequently biopsied. An ROI boundary was manually drawn around the entire lesion in a pharmacokinetic image showing near maximal enhancement (as in FIG. 5a). The patients are enumerated in Table 1, below. The FIG. 5 images are from patient 3. The DCE-MRI time-courses were each analyzed with several pharmacokinetic models.

TABLE 1

| Patient Number | BI-RADS | $K^{trans}$(min$^{-1}$) SM (FXL-c) | $K^{trans}$(min$^{-1}$) SSM (FXR-a) | $k_{ep}$(min$^{-1}$) SM (FXL-c) | $k_{ep}$(min$^{-1}$) SSM (FXR-a) | Pathology Report |
|---|---|---|---|---|---|---|
| 1 | B-4 | 0.073 | 0.147 | 0.389 | 0.249 | DCIS, intermediate nuclear grade |
| 2 | B-4 | 0.110 | 0.180 | 0.452 | 0.447 | IDC, histologic grade II/III; DCIS, intermediate nuclear grade; DCIS ≤ 25% of total tumor mass. |
| 3 | B-4 | 0.087 | 0.131 | 0.161 | 0.147 | IDC present at the edge of the core |
| 4 | B-5 | 0.164 (±0.028) | 0.254 (±0.029) | 0.532 | 0.432 | IDC, histologic grade II/III; DCIS, intermediate nuclear grade; DCIS > 25% of total tumor mass. |
| 5 | B-5 | 0.559 (±0.040) | 1.63 (±0.06) | 1.795 | 2.966 | IDC, histologic grade II/III |
| 6 | B-5 | 0.145 | 0.185 (±0.020) | 0.506 | 0.308 | IDC |
| 7 | B-4 | 0.051 | 0.081 | 0.269 | 0.202 | IDC, unclear grade II. LCIS; moderately differentiated IDC embedded within a larger: benign LCIS |
| 8 | B-5 | 0.033 (±0.005) | 0.034 (±0.006) | 0.106 | 0.053 | LCIS, SF |
| 9 | B-4 | 0.022 | 0.023 | 0.147 | 0.047 | FC |
| 10 | B-4 | 0.051 | 0.058 | 0.306 | 0.155 | FC |
| 11 | B-4 | 0.040 | 0.055 | 0.280 | 0.120 | FC |
| 12 | B-4 | 0.062 | 0.077 | 0.397 | 0.188 | Sclerosed papillary lesion, LCIS |
| 13 | B-4 | 0.027 | 0.028 | 0.048 | 0.039 | FC |
| 14 | B-4 | 0.030 | 0.034 | 0.229 | 0.096 | ADH, SF |
| 15 | B-4 | 0.091 | 0.099 | 0.189 | 0.131 | LCIS, SF, FC |
| 16 | B-4 | 0.078 | 0.087 | 0.188 | 0.130 | LCIS, ADH |
| 17 | B-4 | 0.108 | 0.125 | 0.289 | 0 166 | duct ectasia, ADH |
| 18 | B-4 | 0.060 | 0.066 | 0.133 | 0.090 | SF, sclerosing adenosis |
| 19 | B-4 | 0.048 | 0.050 | 0.185 | 0.086 | FA |
| 20 | B-4 | 0.026 (±0.010) | 0.028 (±0.005) | 0.174 | 0.066 | FA |
| 21 | B-5 | 0.020 | 0.022 | 0.307 | 0.136 | FA |
| 22 | B-4 | 0.016 | 0.016 | 0.436 | 0.078 | FA |

IDC: invasive ductal carcinoma;
DCIS: ductal carcinoma in situ;
LCIS: lobular carcinoma in situ;
SF: stromal fibrosis;
FC: fibrocystic changes;
ADH: atypical ductal hyperplasia;
FA: fibroadenoma.

For the patients/results presented in Table 1, ROI boundaries around each lesion were separately drawn by each of two independent investigators who were blinded to the pathology results. The analyses of these ROI data were also conducted independently by two investigators. The algebraic means of the model parameters returned from each investigator's fitting were computed lesion-by-lesion.

Each of the fittings neglects the small blood water proton signal ($^1H_2O_b$)—thus, these are "first generation" versions. For this situation, the MR exchange system of interest is that for equilibrium transcytolemmal water interchange ($k_{oi}$, and $k_{io}$, FIG. 1). The system's condition is given by the comparison of the equilibrium kinetics, $k=K_{oi}+k_{io}$, with the pertinent MR shutter-speed, $T^{-1}\equiv |R_{1o}-R_{1i}|$, where $R_{1o}$ and $R_{1i}$ are the relaxation rate constants for the $^1H_2O_o$ and $^1H_2O_i$ signals in the absence of exchange. Before CR arrival, $R_{1o}\approx R_{1i}$ and $T^{-1}\ll k$. Though k is finite, and invariant throughout the DCE-MRI study, the system is in the fast-exchange-limit (FXL): the kinetics appear infinitely fast, and the measured tissue $^1H_2O$ $R_1$ is single-valued. As stated above, the Standard Model assumes that the system remains in the FXL throughout the CR bolus passage, so it is referred to also as the FXL-constrained (FXL-c) model (see FIG. 5b). However, as the $CR_o$ concentration increases, $R_{1o}$ becomes increasingly larger than $R_{1i}$ and $T^{-1}$ at least approaches the constant k value. For some period, the measured $R_1$ remains effectively single-valued, and this has been defined to be the fast-exchange-regime (FXR). Admitting departure from the FXL for the FXR may be referred to as FXR-allowed (FXR-a) (see FIG. 5c). Further $CR_o$ increase may lead to the condition where $R_1$ is effectively double-valued: this is referred to as the slow-exchange-regime (SXR). Admitting this is referred to as SXR-allowed (SXR-a) (see FIG. 5d). For the cases here, the results of FXL-c and FXR-a analyses are presented in Table 1. Careful analyses with the SXR-a model suggest that it is incompatible with these data—an example will be seen below. There are a number of potentially variable parameters. For the SM (FXL-c) analyses, the variables were $K^{trans}$ and $v_e$, while for the SSM (FXR-a) analyses, $\tau_i$ was also varied. In terms of the FIG. 1 notation, $K^{trans}=v_ek_{ep}=v_bk_{pe}$, and $\tau_i=k_{io}^{-1}$. The values returned for $K^{trans}$, a measure of the rate of passive CR transfer across the vessel wall, and $k_{ep}$, the unidirectional rate constant for CR intravasation (FIG. 1) are given in Table 1. Sample standard deviation measures of parameter uncertainty from individual fittings are given for some entries. These were determined by multiple Monte Carlo fitting calculations. The $K^{trans}$ and $k_{ep}$ values for the malignant tumors (top seven entries) are larger than those for the benign lesions.

Table 1 indicates that the SM does not completely separate the malignant tumors (top seven entries) from the benign lesions with either the $K^{trans}$ or $k_{ep}$ parameters. However, the SSM significantly increases $K^{trans}$ for every one of the malignant lesions, and for none of the benign tumors, as compared to the SM. Furthermore, though the SSM reduces $k_{ep}$ for both malignant and benign lesions, it does this more for the benign tumors. In embodiments, these changes allow discrimination between the SSM and SM results.

Though neither of the parameters allows the construction of perfect ROC (Receiver Operator Characteristic) plots, the SSM $K^{trans}$ and $k_{ep}$ quantities come very close. These aspects may be seen in the 2D parametric scatter plots of the $K^{trans}$ (ordinate) and $k_{ep}$ (abscissa) values presented in FIG. 6. The ROI values for lesions found by pathology analyses (Table 1) to be solely benign are indicated with triangles, while those with major malignant regions are shown as black circles. The two gray circles with black cores also represent malignant tumors and are discussed below. The results from the SM (FXL-c) analyses are seen in panel a, while those from the SSM (FXR-a) determinations are shown in panel b. The values for patient 5 are so large that they are shown in inset panel c and inset panel d.

In comparing FIG. 6b with 6a, one can note especially the upward movement (increasing $K^{trans}$) of the circles and the leftward movement (decreasing $k_{ep}$) of the triangles, in going from the SM to the SSM. This allows the almost complete separation of these points in FIG. 6b, which is not achieved in any single dimension of either panel. It is important to note that two of the triangles represent B-5 lesions (Table 1): i.e., they were "highly suggestive" false positives. Retaining 100% sensitivity (not missing any malignant tumor), the PPV values for the SM $K^{trans}$, SM $k_{ep}$, SSM $K^{trans}$, and SSM $k_{ep}$ dimensions are: 54%, 39%, 70%, and 70%, respectively. In the FIG. 6b SSM 2D plot, one can draw a dashed quarter-circle of radius 0.19 $\text{min}^{-1}$, that also allows a 78% PPV.

Furthermore, consider the annular region between this and the other concentric quarter-circle, of radius 0.23 $\text{min}^{-1}$. The only two malignant tumors (circles with dark cores within) are those of patients 3 (upper) and 7 (lower). These are cases where the malignant areas are quite small compared with the total tumor area visualized in the biopsy specimen (Table 1). This means that the analyses of whole-tumor ROI-averaged data cause a partial volume dilution of the DCE-MRI parametric values. This can be seen clearly in panels b and c of FIG. 5, which present $K^{trans}$ parametric heat maps of the lesion of patient 3. In the SM (FXL-c) and SSM (FXR-a) maps (panels b and c, respectively), a clear "hot spot" is seen on the posterior lesion edge. The hot spot has $K^{trans}$ values above 0.16 $\text{min}^{-1}$ in the FXR-a map, considerably elevated above the ROI-averaged magnitude (Table 1).

The hot regions of all seven malignant tumors in this population have SSM $K^{trans}$ values exceeding 0.1 $\text{min}^{-1}$. Except for that of patient 17 (upper triangle in FIG. 6b annulus, and which uniquely exhibits ductal dilation (Table 1)), this exceeds the ROI-averaged SSM $K^{trans}$ values of any of the fifteen benign lesions. With FIGS. 5b, 5c, and 5d, parametric maps (heat maps) of four of the seven malignant tumors have been presented in several publications referenced below. Some hot spots can be as small as 2 mm in diameter. In another indication of potential staging power, a plot (not shown) of "hotness" vs. area of the SSM $K^{trans}$ hot spots in the malignant tumors of patients 5, 6, and 7 demonstrates that these two independently measured quantities are very highly positively correlated. The fact that the SXR-a $K^{trans}$ map of the patient 3 lesion (FIG. 5d) does not show increased values relative to the FXL-c map (FIG. 5b)—and in fact obliterates the hot spot—is an example of the SXR-a model incompatibility with these data.

Figure 6:
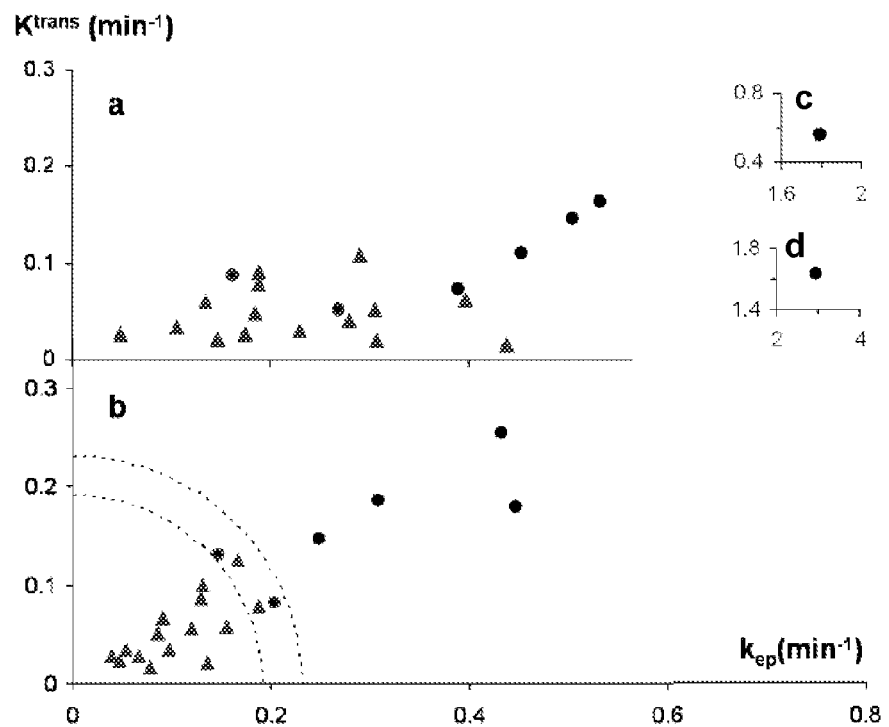
FIG. 6 illustrates 2D scatter plots of (a) the Standard Model, and (b) the Shutter-Speed Model (FXR-a) results. The ordinates measure the $K^{trans}$ and the abscissae the $k_{ep}$ parameters. The black circles mark the positions for regions of interest (ROIs) of lesions that were found by biopsy/pathology to have large malignant fractions, while the triangles are those for lesions found to be solely benign. An outlier is plotted in insets c and d. Dashed concentric quarter-circles are drawn with radii of 0.19 and 0.23 min$^{-1}$. The points for two patients are marked as gray circles with black cores. These represent lesions with only very small malignant fractions.

The $K^{trans}$ and $k_{ep}$ values are rather well correlated in FIG. 6, particularly in panel b. The positions of the panel a and b insets are placed with constant coordinate aspect ratios. Thus, one can visually include the inset points in the correlations. The slope of a line drawn through the points represents the mean $v_e$ value of these lesions. Such a line for FIG. 6b has a slope near 0.5.

These results suggest a potential breast cancer screening protocol in accordance with an embodiment herein. The first step of such a protocol would be a clinical examination and/or mammography. A positive result (B-4 or B-5), or suspicion of a mammographically occult lesion, would occasion referral for diagnostic MRI that includes DCE. The radiologist can circumscribe an ROI from the DCE image showing the greatest enhancement. Alternatively, this can be automated (ex., Jim 4.0 software; Xinapse Systems; Thorpe Waterville, UK). The computer can very quickly (few seconds) conduct SM and SSM analyses on the mean ROI signal time-course data and produce SSM $K^{trans}$ and $k_{ep}$ values, which can be compared with 2D scatter plots such as those in FIG. 6b. If a patient's point turns out to be in the annulus between the quarter-circles in FIG. 6b, the radiologist could proceed to read $K^{trans}$ parametric lesion maps made from the same DCR-MRI data, though these require more computational time. Hot spots above 0.1 $min^{-1}$ would be very suspicious for malignancy.

Some oncologists advocate a separate regimen for a malignant ductal carcinoma in situ (DCIS) tumor, possibly simply following it instead of immediate surgery, while others urge excision. The only solely DCIS case in the discussed patient population is that of patient 1. Her position in FIG. 6b is the black point closest to the outer quarter-circle. In fact another concentric quarter-circle of radius 0.3 $min^{-1}$ would isolate this point. Its position could be "followed" or tracked over a period of time to see if it moves up and to the right. Inside the inner quarter-circle, most of the benign LCIS lesions are found in the upper right sector, while all of the FA lesions are found near the bottom.

In the analyses so far, pseudo-absolute parameter values have been employed. The SSM success suggests that neglect of equilibrium transcytolemmal water exchange effects may constitute the most significant systematic error in Standard Model DCE-MRI pharmacokinetic analyses.

Figure 7:
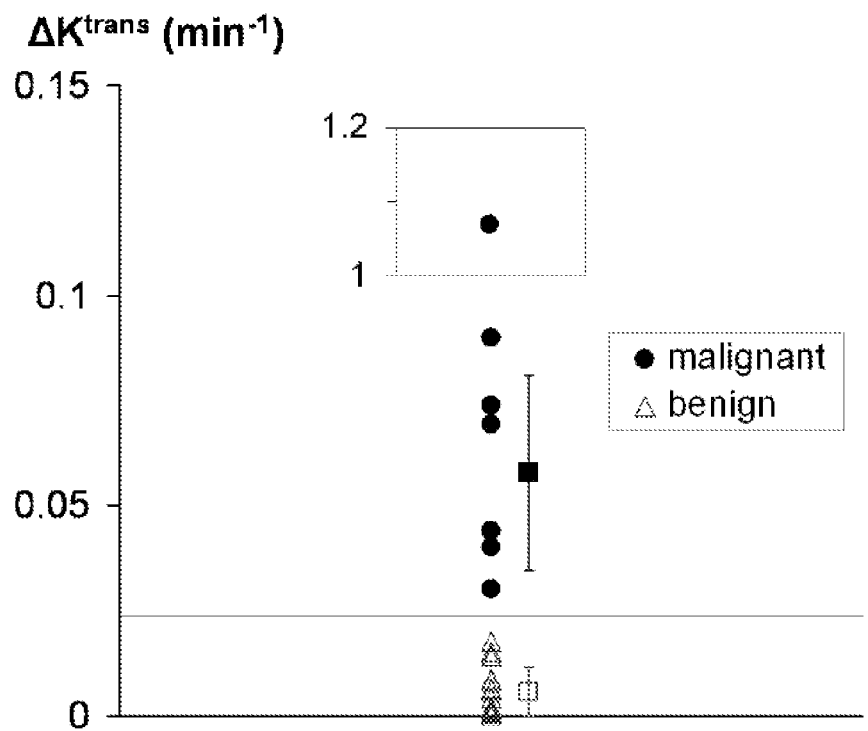
FIG. 7 illustrates a 1D scatter plot. The ordinate, $\Delta K^{trans}$, is $[K^{trans}(SSM) - K^{trans}(SM)]$: SSM is FXR-a and SM is FXL-c. The values for the lesion ROIs of all 22 subjects are shown. Those proven malignant are given as filled black circles (these include the two FIG. 6 gray circles with black cores), while those found solely benign are indicated with triangles. The group mean $\Delta K^{trans}$ values are indicated with open and filled black squares on the right. Error bars represent (SD) values within each category. One malignant lesion outlier is plotted in an inset, and is excluded from the SD calculation. The horizontal cut-off line drawn at 0.024 min$^{-1}$ cleanly separates the two lesion groups.

For screening purposes, the most striking aspect of the Table 1 and FIG. 6 results is that every one of the malignant tumor ROI $K^{trans}$ values (dark circles) is clearly decreased by the SM analysis, while every one of the benign lesion ROI values (triangles) is not. This is seen even more clearly in FIG. 7, which presents the 1D scatter plot for $\Delta K^{trans}[\equiv K^{trans}(SSM) - K^{trans}(SM)]$. There is a wide gap between all seven of the dark circles [group mean, 0.06 min–1 (excluding the inset point)], and all 15 of the triangles. The latter set clusters very near zero [group mean, 0.006 min–1]. A clean cut-off line is drawn at 0.024 $min^{-1}$. Since the only difference between these two models is the allowance for the effect on the NMR signal of finite equilibrium transcytolemmal water exchange kinetics, the NMR shutter-speed effect, this suggests that it is significant (for the $K^{trans}$ magnitude) with the capillary wall permeability obtained for the vascular beds of only malignant breast tumors. Thus, this is very encouraging that analyses of DCE-MRI ROI data first with one pharmacokinetic model and then with the other (which is still accomplished in only seconds) can lead to extremely high specificity in cancer screening. Here, the positive criterion of $\Delta K^{trans} > 0.025$ $min^{-1}$ yields 100% PPV.

Apparently, in the vascular beds of malignant breast tumors only, the interstitial ("outside") CR concentration, $(CR_o)$, transiently rises to sufficient values during the bolus passage and the equilibrium transcytolemmal water exchange system transiently departs the FXL to sufficient extent and/or for sufficient duration to substantially invalidate the SM $K^{trans}$ determination. The SSM interpretation is that, during the bolus passage through malignant lesions, the relaxographic $T^{-1}$ value for the transcytolemmal water exchange process, $|R_{1o}-R_{1i}|$, transiently approaches or exceeds that for the unchanging exchange rate constant, $k_{io}+k_{oi}$, (in vivo studies are isothermal) sufficiently for the system to enter at least the fast-exchange regime (FXR), but probably not also the slow-exchange-regime (SXR). $R_{1o}$ increases with $CR_o$, while $R_{1i}$, remains constant. This is a manifestation of the varying equilibrium competition for interstitial water molecules between diamagnetic cytoplasmic spaces and paramagnetic interstitial CR molecules (FIG. 1). Informative estimates can be made by comparison of the Table 1 patients 8/4 benign/malignant lesion pair, with SSM $K^{trans}$ 0.034 and 0.254 $min^-$ 1, respectively. For one of the SSM (FXR-a) fittings of each, the $(v_e, \tau_i)$ parameters returned are similar: (0.60, 0.40 s), and (0.69, 0.39 s) for benign and malignant, respectively. Thus, the unidirectional rate constants for water cellular entry $[k_{oi} \approx (v_e^{-1}-1)\tau_i^{-1}]$ are similar (1.7 and 1.2 $s^{-1}$, respectively), constant, and not infinitely large. However, before the arrival of interstitial $CR_o$, the transcytolemmal water exchange appears infinitely fast in the NMR signal because $T^{-1}$ is almost negligible. The interstitial water molecules encounter no paramagnetic $CR_o$ molecules before entering a diamagnetic cytoplasm. However, as $CR_o$ increases, the rate constant for interstitial water CR encounter, $[(CR_o)/(H_2O_o)]\tau_M^{-1}$, also increases $[\tau_M^{-1}=k_M$ in FIG. 1]. While, for the benign lesion $CR_o$ maximizes at 0.52 mM (at ~7.5 minutes), this is 1.6 mM (at ~3.5 minutes) for the malignant tumor. Thus, $[(CR_o)max/(H_2O_o)]\tau_M^{-1}$ values are 104 and 313 $s^{-1}$ for the benign and malignant lesions, respectively. The interstitial water concentration $(H_2O_o)$ was 50 M and the mean water lifetime on the CR, $\tau_M$, was $10^{-7}$ s. At maximum $CR_o$, an interstitial water molecule in the benign lesion encounters a paramagnetic CR molecule on average 60 times (104/1.7) before it enters a diamagnetic cell; sufficient, apparently, for the SM 40% $v_e$ underestimation. While in the malignant tumor, this happens 260 times (313/1.2) on average; more than four times as often. This is sufficient to cause significant $K^{trans}$ underestimations if it is neglected.

For the expanded data set, a total of 74 patients underwent clinical breast MRI protocols and had 77 contrast-enhanced lesions (3 patients presented 2 lesions each) radiologically classified in the BIRADS (Breast Imaging Reporting and Data System) 4 (B-4, suspicious, n=67) or 5 (B-5, highly suggestive of malignancy, n=10) categories based on lesion morphology and qualitative enhancement kinetics assessment. These clinical interpretations led to biopsy referrals. The research DCE-MRI data acquisitions were IRB-approved. The data from 6 patients were collected as part of a combined MRI/MRS protocol prior to excisional or core biopsy. Those from the other 68 patients (71 lesions) were acquired during clinically scheduled MRI-guided preoperative needle localization or core biopsy procedures, just before needle insertions.

The study was conducted at 1.5T using a body transmit and a four- or seven-channel phased-array bilateral breast receive RF coils. A 3D SPGR pulse sequence was used to acquire 12-20 serial sagittal image volume sets continually, spatially covering the whole breast with the suspicious lesion to be biopsied. Other parameters included 10° or 30° (for the 6 patients) flip angle, 2-5 ms TE, 6-9 ms TR, 3 mm section thickness, 20-24 cm FOV. Depending on the breast size, 16-36 image sections were acquired for each set, resulting in inter-sampling intervals of 13-42 seconds. At the start of the second volume set acquisition, Gd CR was delivered intravenously [0.1 mmol/kg at 2 mL/s]. ROIs circumscribing the enhanced lesion and within an axillary artery produced the tumor signal intensity and arterial input function (AIF) time-courses, respectively. Three reliable individual AIFs were measured, which were interpolated with an empirical expression (3) and averaged to generate a mean AIF. The tumor ROI and mean AIF signal time-courses were then subjected to both SM and (fast-exchange-regime-allowed) SSM analyses, which were blinded from the pathology. Receiver-operating-characteristic (ROC) curves were used to evaluate pharmacokinetic parameter diagnostic accuracies, and the areas under the curve (AUCs) were compared using a Bootstrap nonparametric test.

Upon pathology, only 18 lesions (10 B-4 and 8 B-5) were found malignant and the other 59 (57 B-4 and 2 B-5) benign.

Though the clinical MRI protocol sensitivity is 100% (no false negatives), its PPV is only 23%. The SSM $K^{trans}$ ROC AUC (0.973) is significantly (p=0.032) greater than that for the SM $K^{trans}$ (0.929). Similar results were obtained for other strong biomarkers: $k_{ep}$ ($=K^{trans}/v_e$, the unidirectional CR intravasation rate constant) [SSM AUC=0.960, SM AUC=0.861, p=0.006] and $[(K^{trans})^2+k_{ep}^2]^{1/2}$ [SSM AUC=0.970, SM AUC=0.887, p=0.009]. Maintaining 100% sensitivity, the diagnostic specificities of the SM ROI $K^{trans}$, $k_{ep}$, and $[(K^{trans})^2+k_{ep}^2]^{1/2}$ are 47%, 42%, and 51%, while those for the corresponding SSM parameters are 76%, 61%, and 75%, respectively; each biomarker used as a binary classifier. The SM and SSM $v_e$ ROC curve AUCs are 0.555 and 0.615, respectively, suggesting that $v_e$ is a poor diagnostic marker.

FIG. 3 (discussed partially above) plots ROI delta $K^{trans}$ for all lesions. Note the ordinate scale break. Each column represents one pathology category (from left to right): 1) invasive ductal carcinoma (IDC)/ductal carcinoma in situ (DCIS) mixture, 2) IDC/invasive lobular carcinoma (ILC) mixture, 3) IDC, 4) DCIS, 6) IDC/lobular carcinoma in situ (LCIS) mixture, and 9) ILC, for the malignant group (circles); 5) tubular adenoma, 7) LCIS, 8) atypical lobular hyperplasia, 10) atypical ductal hyperplasia, 11) stromal fibrosis, 12) benign parenchyma, 13) fibrocystic changes, 14) papillary lesions, 15) miscellaneous benign conditions, 16) fibroadenomatoid changes, and 17) fibroadenoma, for the benign group (triangles). The categories are ranked roughly in order of decreasing mean delta $K^{trans}$ from left to right. Consistent with the previous smaller population study, the delta $K^{trans}$ biomarker represents the strongest binary classifier for benign and malignant group separation, with its ROC AUC=0.990, and 88% specificity for 100% sensitivity.

The SSM DCE-MRI ROI pharmacokinetic parameters consistently perform better than those from SM DCE-MRI and the commonly used clinical MRI protocols for benign and malignant discrimination within this group of 77 suspicious breast lesions. If the simple ROI delta $K^{trans}$ analyses had been integrated into clinical practice, as many as 52 benign lesions (68% of the total population) could have been spared the biopsy procedures. As expected from the earlier study, the malignant lesions cluster almost exclusively on the left of FIG. 3, while the benign lesions are almost all to the right—the axes are independent. The solid cut-off line value, delta $K^{trans}$=0.028 min$^{-1}$, is very close to that for 100% specificity in the smaller population. It yields only one false positive (the sole tubular adenoma) and one false negative (the sole ILC) lesion. A more lenient, dashed cut-off line can be drawn at delta $K^{trans}$=0.012 min$^{-1}$ to avoid any false negative and still incur only 14 benign biopsies. But, even these might be avoided. The likely reason for a malignant lesion ROI delta $K^{trans}$ to fall between the solid and dashed cut-off lines is because of partial volume averaging in the ROI analyses. Consistent with this, the ILC had the very large value of 5 cm as the greatest enhanced ROI dimension. Its pixel-by-pixel SSM $K^{trans}$ map (not shown) features hot spots ($K^{trans}$>0.18 min$^{-1}$) only in the posterior rim region. Though these are diluted by a very large area of small $K^{trans}$ values in the ROI, they confirm the lesion as malignant. This suggests that delta $K^{trans}$ or SSM $K^{trans}$ maps (parametric heat maps) should be made when an ROI delta $K^{trans}$ falls between the solid and dashed lines.

Other analysis methods may be used to further distinguish the data, such as points falling between delta $K^{trans}$ thresholds. For example, the median $K^{trans}$ difference, delta (median $K^{trans}$)[SSM median $K^{trans}$−SM median $K^{trans}$], may be plotted (ordinate) vs. the change in maximum histographic probability (amplitude) (abscissa), delta Amp [SSM amplitude−SM amplitude]. Such an operation indicates a significant negative linear correlation (Pearson correlation=−0.82, p=0.0018) for the benign lesions, while the malignant lesions exhibit an almost orthogonal correlation. The ILC (identified for example in FIG. 3) cannot be distinguished from the benign group with simple ROI delta $K^{trans}$ analyses. However, using quadratic discrimination analysis, the benign and malignant lesions can be completely separated (100% sensitivity and 100% specificity) by the solid partition curve with no misclassification.

Though the ROI delta $K^{trans}$ biomarker achieves high specificity for benign/malignant breast lesion discrimination, the partial volume averaging effects of ROI analyses can cause overlap in ROI pharmacokinetic parameter values, and thus prevent clearer separation of the two groups. Pharmacokinetic parametric mapping and histogram analyses thus may further improve discrimination. Such analyses are especially important when the lesion ROI biomarker value falls in the vicinity of a binary classifier cut-off value. Thus, it is beneficial to acquire DCE-MRI data with sufficient SNR, since this ensures reliable pixel signal time-course curve fitting. The negative linear correlation of the benign lesions and the orthogonal behavior of the malignant lesions are quite interesting. Compared to malignant lesions that can have noticeable median $K^{trans}$ increases (shutter-speed (SS) histographic shifts) without significant histographic maximum probability changes (SS broadening), the areas in benign lesions where increased blood vessel CR permeability incurs SS effects, if any, are smaller. Considerable SS histographic broadening is associated with even minuscule SS histographic shifting.

Further details regarding the materials and methods used with respect to various embodiments described herein as well as details regarding some of the MRI data acquisitions and analyses may be found in Li, et al., Dynamic NMR Effects in Breast Cancer Dynamic-Contrast-Enhanced MRI, PNAS, Vol. 105, No. 46, 17937-17942 (2008) (and Supporting Online Material); Huang, et al., The MR Shutter-Speed Discriminates Vascular Properties of Malignant and Benign Breast Tumors In Vivo, PNAS, Vol. 105, No. 46, 17943-17948 (2008); Li, et al., Shutter-Speed Analysis of Contrast Reagent Bolus-Tracking Data: Preliminary Observations in Benign and Malignant Breast Disease, Magn. Reson. Med., 53:724-729 (2005); and Yankeelov, et al., Evidence for Shutter-Speed Variation in CR Bolus-Tracking Studies of Human Pathology, NMR Biomed., 18:173-185 (2005), the entire disclosures of which are hereby incorporated by reference.

In accordance with embodiments herein, certain steps may be taken, even in the clinical setting, to improve the precision, the accuracy, and/or the diagnostic richness of the SSM DCE-MRI pharmacokinetic parameters. Such modifications may, for example, decrease the random error scatter in the FIGS. 6 and 7 point clusters. This may allow further discrimination of pathology sub-types.

The DCE-MRI time-course acquisitions discussed herein were prescribed for radiological considerations and were truncated. Increasing this period would likely improve accuracy and precision of the benign lesion parameters. For these ROIs, the maximum $R_1$ value is rarely reached in the no more than seven minutes usually allowed. This is the likely source of abnormally large $v_e$ values for some benign tumors. Increasing the period to 15 minutes may help define the shape of the time-course, even for malignant tumors.

The DCE-MRI acquisitions for the data described herein were not particularly exchange sensitive. Even so, exchange effects seem to facilitate very high discrimination of malignant from benign breast tumors.

The tissue $R_{10}$ values (the pre-CR $^1H_2O$ longitudinal relaxation rate constants) may be mapped, and not simply assumed as they were herein. Individual AIFs may be used as well. A reference tissue method, or an automated AIF determination (ex., Jim 4.0 software; Xinapse Systems; Thorpe Waterville, UK) may be used.

Increased temporal resolution may be achieved without sacrificing spatial resolution or signal-to-noise. Parallel RF excitation/acquisition may be useful for achieving such increased temporal resolution. With good definition of the DCE time-course first-pass leading edge, the second generation SSM (BALDERO (Blood Agent Level Dependent and Extravasation Relaxation Overview)) analysis, which accounts for blood $^1H_2O$ signal pharmacokinetic behavior, may be used to also determine $v_b$ and $k_{bo}$ values. It is anticipated that tumor $v_b$ values will have significant diagnostic value. Furthermore, $v_b k_{bo}$ is the transendothelial water permeability coefficient surface area product, $P_W S'$, where $S'$ is the total capillary bed surface area. The ratio $P_W S'/P_{CR} S'$ would be the intensive property $P_W/P_{CR}$. The value of the CR permeability coefficient surface area product ($P_{CR} S'$) may be factored from the $K^{trans}$ parameter using the blood flow value, which may also be determined from DCE-MRI data.

The DCE-MRI pharmacokinetic images may also be spatially registered to correct for patient motion.

Image acquisition without —$^1H_2C$— suppression may yield signal intensities much more amenable to precision parametric mapping. The maps require sufficient acquisition contrast-to-noise ratio because pixel-by-pixel analytical modeling is more susceptible to noise. However, care must be taken to avoid contamination of $^1H_2O$ by unsuppressed —$^1H_2C$—.

In embodiments, the shutter-speed model may be enhanced by adding a factor for putative $T_2^*$ (transverse relaxation) signal quenching. In an embodiment, there is provided a direct application of a $T_2^*$ reduction factor to the interstitial water signal in the Ernstian MR steady-state DCE-MRI model expression. Assuming the greatest $T_2^*$ reduction will return $K^{trans}$ and $v_e$ values for the tumor region of interest about 35% and 15% greater, respectively, than one would find when ignoring this effect. For normal-appearing tissues, these are 11% and 17% greater, respectively. Thus, applying the factor further distinguishes normal tissue from the tumor ROI. FIG. 8 illustrates this relationship.

The SXR-a SSM includes $T_2^*$ neglect and therefore underestimates $K^{trans}$ and $v_e$ to the extent that there is a disproportionate relaxation of compartmental water signals. Embodiments herein provide a way of testing to see if the blood and interstitial water signals have been edited from the detected signal (that is, SXR-a is inappropriate).

DCE-MRI pharmacokinetic modeling usually ignores potential $^1H_2O$ signal reduction due to transverse relaxation ($T_2^*$) effects. Most clinical DCE-MRI applications employ a contrast reagent (CR) dose of 0.1 mmol/kg which may produce a blood plasma CR concentration above 5.0 mM at its peak during the bolus passage. Here, using exemplary prostate DCE-MRI data, a potential $T_2^*$ effect on DCE-MRI model parameter values is described, by using a water exchange ("shutter-speed") model along with a simplified factor to account for putative $T_2^*$ signal quenching.

Prostate $H_2O$ MRI data were acquired with a Siemens TIM Trio (3T) system under an IRB approved protocol. RF transmitting was through the whole body coil and RF receiving was with a combination of Spine Matrix and flexible Body Matrix RF coils. The DCE-MRI sequence employed a 3D TurboFLASH sequence with a 256*144*16 matrix size and a 360*203 mm² field of view, resulting in an in-plane resolution of 1.4*1.4 mm². Other parameters are: slice thickness: 3 mm; TR/TE/FA: 5.42 ms/1.56 ms/15°, imaging intersampling interval: 4.16 seconds. Any $T_2^*$-induced signal reduction is assumed to be proportional to $[\exp(-(r_2^*(CR)+R_{20})\cdot TE)]$, applying to the $^1H_2O$ signal from the CR-occupied compartment. For the data here, the most influential CR-containing compartment is the prostate interstitium. Thus, $r_2^*$ and CR represent the interstitial CR transverse relaxivity and concentration, respectively. Since susceptibility effects cross compartmental boundaries, surely $r_2^*$ also has a contribution from capillary blood plasma CR. This $T_2^*$-reduction factor is then directly applied to the interstitial $^1H_2O$ signal in the Ernstian MR steady-state DCE-MRI model expression. Parameter uncertainties were determined with sets of Monte Carlo simulations carried out for each ROI-averaged $^1H_2O$ signal with increasing $T_2^*$ quenching accounted for by choosing an increasing $r_2^*$ value (mM$^{-1}$s$^{-1}$): 0 (no quenching), 5 (a literature value), 20 (an estimated blood plasma value at 3T), or 40. For each $r_2^*$ and each ROI data set, 200 simulation runs were performed with Gaussian noise ($\mu=0$, $\sigma=0.08$) directly added to the normalized ROI data time-course. This resulted in a simulated time-course with a signal-to-noise ratio (SNR) slightly better than that from a single pixel. Random initial guess values were evenly distributed within the parameter space for each simulation fitting.

FIG. 9a inset shows a transverse pelvic DCE image slice (anterior up/inferior perspective, ~34 seconds post CR injection) of a research subject. Two ROIs are indicated within the prostate gland: one in an area of retrospectively-confirmed prostate cancer, left; and the other in contralateral normal-appearing prostate tissue, right. FIG. 9a plots the arterial input function obtained from an ROI in a femoral artery. Its magnitude was adjusted using a custom-written numerical approach and an obturator muscle ROI for reference tissue. The time-course from the first-pass (includes the initial peak) was used to estimate blood volume fraction. Color-matched tissue data time-courses (points) and representative fittings (curves) are seen in FIG. 9b.

FIG. 8 shows how the $K^{trans}$ (volume fraction CR transfer rate constant product, top) and $v_e$ (extracellular, extravascular space, EES, volume fraction, bottom) fitting results would change if increasing interstitial $^1H_2O$ $T_2^*$ quenching is assumed. With $K^{trans}$ values this large, the algorithm is effectively a two-site (interstitium/cytoplasmae) exchange model, and the $T_2^*$-induced signal reduction is applied to only the EES signal. As noted above, assuming the greatest $T_2^*$ reduction ($r_2^*=40$ mM$^{-1}$s$^{-1}$) will return $K^{trans}$ and $v_e$ values for the tumor ROI about 35% and 15% greater, respectively, than one would find ignoring this effect. For the normal-appearing tissue, these are 11% and 17% greater, respectively. Conversely, the usual literature analysis includes transverse relaxation neglect (by effectively assuming $r_2^*=0$) and thus underestimates $K^{trans}$ and $v_e$ to the extent that there is disproportionate relaxation of compartmental $^1H_2O$ signals.

The analysis used here is based on an inherently three-site model, but multi-step recursive fittings would eventually return a zero (within error) blood volume fraction ($v_b$) for the tumor tissue. This is not because $v_b$ is actually zero, but only because it is indeterminate due to the very CR-permeable capillary wall. The blood $^1H_2O$ signal makes a contribution indistinguishable from that of the EES. Thus, it may be better to use an only two-site model. For consistency, the same two-site model is also used for the normal appearing tissue ROI. The current analysis is conservative in estimating EES signal $T_2^*$-quenching effects. Interestingly, however, the extracted parameters move exactly in the direction seen comparing analyses with the fast-exchange-regime (FXR)-allowed two-site shutter-speed model with the slow-exchange-regime (SXR)-allowed version. The former neglects a distinguishable interstitial $^1H_2O$ signal contribution, which is reduced by exchange and may also be at least partially $T_2^*$-quenched. For a tumor blood volume estimation using DCE-MRI with extravasating CR, it is prudent to use a lower CR dose.

Any one or more of various embodiments previously discussed may be incorporated, in part or in whole, into a computing device or a system. A suitable computing device may include one or more processors for obtaining/receiving data, processing data, etc. One or more of the processors may be adapted to perform methods in accordance with various methods as disclosed herein. A computing device may also include one or more computer readable storage media.

Any one or more of various embodiments as previously discussed may be incorporated, in part or in whole, into an article of manufacture. In various embodiments and as shown in FIG. 10, an article of manufacture 1000 may comprise a computer readable medium 1010 (a hard disk, floppy disk, compact disk, etc.) and a plurality of programming instructions 1020 stored in computer readable medium 1010. In various ones of these embodiments, programming instructions 1020 may be adapted to program an apparatus, such as an MRI device or a processor within or separate from an MRI device, to enable the apparatus to perform one or more of the previously-discussed methods.

In an embodiment, a computing device/system may be configured to receive MR images through any of a variety of communication schemes (wired or wireless), to analyze the data as described herein to classify the tissue that was the subject of the MR image, and to display/transmit the results. The computing device/system may be configured to receive MRI data from an integrated MRI device or from a separate MRI device in communication electronically. The computing device/system may then display the analysis results on an integrated display, or may send the results to a separate computing device, using any suitable electronic communication mechanism, for separate display and potentially further analysis.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A computer implemented method for tissue characterization based on water kinetics, the method comprising:
    including one or more processors for receiving DCE-MRI time course data for tissue region wherein a contrast reagent is administered prior to imaging; identifying a region of interest from the DCE-MRI data for further analysis;
    analyzing the data for the region of interest using computer implemented software to produce a SM Ktrans value, where the water exchange between cells or blood and interstitial spaces is assumed to be substantially infinitely fast;
    analyzing the data for the region of interest using computer implemented software to produce a SSM Ktrans value, where the water exchange between cells or blood and interstitial spaces is assumed to have a finite speed resulting from interaction with the contrast reagent; and
    determining a ΔKtrans value comprising SSM Ktrans-SM Ktrans.

2. The method of claim 1, wherein the determined $\Delta K^{trans}$ value is compared to a pre-determined threshold to determine if the $\Delta K^{trans}$ value is above or below the pre-determined threshold.

3. The method of claim 2, wherein the predetermined threshold is between about 0.02 to about 0.03 $min^{-1}$.

4. The method of claim 3, wherein if the $\Delta K^{trans}$ value is above the predetermined threshold, the region of interest is determined to comprise malignant tissue.

5. The method of claim 1, wherein the region of interest is located in the breast of a human.

6. The method of claim 5, wherein the method is performed before biopsy.

7. The method of claim 1, where the identifying a region of interest for further analysis is done manually.

8. The method of claim 1, where the identifying a region of interest for further analysis is done automatically.

9. The method of claim 1, further comprising spacially registering the image data to correct for a patient's movement during imaging.

10. The method of claim 1, wherein the received image data is acquired using unsupressed —$^1H_2C$—.

11. The method of claim 1, further comprising:
    analyzing the data for the region of interest to produce a SSM $K_{ep}$ value, where the water exchange between the cells or blood and interstitial spaces is assumed to have a finite speed resulting from interaction with the contrast reagent; and
    plotting SSM $K^{trans}$ v. SSM $K_{ep}$, wherein the radius of a circle centered at the origin is used to establish a pre-determined $K_{ep}$ threshold.

12. The method of claim 11, wherein the pre-determined $K_{ep}$ threshold comprises values of from about 0.19 $min^{-1}$ to about 0.25 $min^{-1}$.

13. The method of claim 12, wherein if the plotted value for SSM $K^{trans}$ v. SSM $K_{ep}$ is above the $K_{ep}$ threshold, the region of interest is determined to comprise malignant tissue.

14. A computer-implemented method for tissue characterization based on water kinetics, the method comprising:
    including one or more processors for receiving DCE-MRI time-course data for a tissue region, wherein a contrast reagent is administered prior to imaging;
    identifying a region of interest from the DCE-MRI data for further analysis;
    analyzing the data for the region of interest using computer implemented software to produce a SM Ktrans value, where the water exchange between cells or blood and interstitial spaces is assumed to be substantially infinitely fast;
    analyzing the data for the region of interest using computer implemented software to produce a SSM Ktrans value and a SSM Kep value, where the water exchange between cells or blood and interstitial spaces is assumed to have a finite speed resulting from interaction with the contrast reagent;
    determining a ΔKtrans value comprising SSM Ktrans-SM Ktrans;
    determining whether the ΔKtrans value is below a pre-determined threshold;
    plotting SSM Ktrans v. SSM Kep, wherein the radius of a circle centered at the origin is used to establish a predetermined threshold; and determining whether the plotted value is above that threshold.

15. The method of claim 14, wherein the pre-determined $\Delta K^{trans}$ threshold is between about 0.02 to about 0.03 $min^{-1}$.

16. The method of claim 15, wherein the pre-determined SSM $K^{trans}$ v. SSM $K_{ep}$ threshold comprises values above from about 0.19 $min^{-1}$ to about 0.25 $min^{-1}$.

17. The method of claim 16, further comprising spacially registering the image data to correct for a patient's movements during imaging.

18. The method of claim 16, wherein the received image data is acquired using unsupressed $-^1H_2C-$.

19. The method of claim 16, wherein the received time-course data is taken over a period of time greater than about 7 minutes.

20. A system for tissue characterization based on water kinetics, the system comprising:
  a computing device configured to receive DCE-MRI time-course data for a tissue region, analyze the data, and report the results of the analysis for display,
    wherein analyzing the data comprises:
      obtaining a SM $K^{trans}$ value, where the water exchange between cells or blood and interstitial spaces is assumed to be substantially infinitely fast;
      obtaining a SSM $K^{trans}$ value, where the water exchange between cells or blood and interstitial spaces is assumed to have a finite speed resulting from interaction with contrast reagent; and
      determining a difference between the SM $K^{trans}$ value and the SSM $K^{trans}$ value.

* * * * *